(12) United States Patent
Kim et al.

(10) Patent No.: US 12,290,085 B2
(45) Date of Patent: May 6, 2025

(54) FEED ADDITIVE COMPOSITION AND FEED COMPOSITION COMPRISING THE SAME

(71) Applicant: CJ CHEILJEDANG CORPORATION, Seoul (KR)

(72) Inventors: Young Jung Kim, Suwon-si (KR); Je Hun Kim, Seoul (KR); Sung Hun Kim, Siheung-si (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 973 days.

(21) Appl. No.: 17/298,281

(22) PCT Filed: Oct. 8, 2019

(86) PCT No.: PCT/KR2019/013203
§ 371 (c)(1),
(2) Date: May 28, 2021

(87) PCT Pub. No.: WO2020/111497
PCT Pub. Date: Jun. 4, 2020

(65) Prior Publication Data
US 2022/0015392 A1    Jan. 20, 2022

(30) Foreign Application Priority Data
Nov. 30, 2018  (KR) .................. 10-2018-0153029

(51) Int. Cl.
| | | |
|---|---|---|
| *A23K 20/105* | (2016.01) | |
| *A23K 20/111* | (2016.01) | |
| *A23K 20/142* | (2016.01) | |
| *A23K 20/158* | (2016.01) | |
| *A23K 20/20* | (2016.01) | |
| *A23K 50/30* | (2016.01) | |
| *A61K 9/00* | (2006.01) | |
| *A61K 31/19* | (2006.01) | |
| *A61K 31/191* | (2006.01) | |
| *A61K 31/198* | (2006.01) | |
| *A61K 31/405* | (2006.01) | |

(52) U.S. Cl.
CPC .......... *A23K 20/105* (2016.05); *A23K 20/142* (2016.05); *A23K 50/30* (2016.05); *A61K 9/0056* (2013.01); *A61K 31/19* (2013.01); *A61K 31/191* (2013.01); *A61K 31/198* (2013.01); *A61K 31/405* (2013.01)

(58) Field of Classification Search
CPC .. A23K 20/105; A23K 20/142; A23K 20/111; A23K 20/20; A23K 20/158; A61K 31/19; A61K 31/191; A61K 31/198; A61K 9/0056; A61K 31/405; Y02P 60/87; A23V 2002/00; A23V 2250/063; A23V 2250/0632; A23V 2250/0648; A23V 2250/065; A23V 2250/0654
See application file for complete search history.

(56) References Cited

U.S. PATENT DOCUMENTS

| | | |
|---|---|---|
| 6,447,834 B1 | 9/2002 | Kazuo |
| 2003/0235646 A1 | 12/2003 | Nelssen et al. |
| 2004/0175447 A1 | 9/2004 | Murano et al. |
| 2013/0046018 A1 | 2/2013 | Romero et al. |
| 2013/0203712 A1 | 8/2013 | Adams et al. |
| 2018/0118657 A1 | 5/2018 | Adams et al. |
| 2018/0250309 A1 | 9/2018 | Asmis |

FOREIGN PATENT DOCUMENTS

| | | | |
|---|---|---|---|
| CN | 1558722 A | | 12/2004 |
| CN | 1642440 A | | 7/2005 |
| CN | 102406082 A | | 4/2012 |
| CN | 102578387 A | * | 7/2012 |
| CN | 102919607 A | | 2/2013 |
| CN | 103037692 A | | 4/2013 |
| CN | 105815549 A | | 8/2016 |
| CN | 106819559 A | * | 6/2017 |
| CN | 107041460 A | | 8/2017 |
| CN | 107095071 A | | 8/2017 |
| CN | 107259179 A | | 10/2017 |
| CN | 107711612 A | | 2/2018 |
| EP | 1430787 A1 | | 6/2004 |
| EP | 1994835 A1 | | 11/2008 |
| JP | H04299942 A | | 10/1992 |
| JP | H0549408 B2 | | 7/1993 |
| JP | H05176688 A | | 7/1993 |
| JP | H05219898 A | | 8/1993 |
| JP | H0775525 B2 | | 8/1995 |
| JP | 2002034467 A | | 2/2002 |
| JP | 2002034468 A | | 2/2002 |
| JP | 2013526580 A | | 6/2013 |

(Continued)

OTHER PUBLICATIONS

English translation of the description of CN-106819559-A. (Year: 2024).*
English translation of the claims of CN-106819559-A. (Year: 2024).*
English translation of CN-102578387-A, https://patents.google.com/patent/CN102578387A/en?oq=CN102578387A, Assessed on Jul. 11, 2024. (Year: 2024).*
Office Action issued Mar. 25, 2024 of KR Patent Application No. 10-2023-0190099.
Beaten Knowledge, Japan Communication, vol. 81, Japan, San Planner, Jan. 1, 2016, 4 pp.

(Continued)

*Primary Examiner* — Samantha L Shterengarts
*Assistant Examiner* — Sagar Patel
(74) *Attorney, Agent, or Firm* — CANTOR COLBURN LLP

(57) ABSTRACT

Provided are a feed additive composition and a feed composition including the same. The feed additive composition includes ursolic acid and/or maslinic acid, and the feed composition includes the feed additive composition.

12 Claims, No Drawings

(56) References Cited

FOREIGN PATENT DOCUMENTS

| | | | |
|---|---|---|---|
| JP | 2016000707 A | 1/2016 |
| JP | 2016199536 A | 12/2016 |
| JP | 2017109942 A | 6/2017 |
| KR | 1020040093151 A | 11/2004 |
| KR | 1020140146307 A | 12/2014 |
| KR | 1020160060586 A | 5/2016 |
| KR | 1020160119273 A | 10/2016 |
| WO | 2003028475 A1 | 4/2003 |
| WO | 2009034151 A1 | 3/2009 |
| WO | 2010132776 A1 | 11/2010 |
| WO | 2017/041077 A1 | 3/2017 |
| WO | 2019055280 A1 | 3/2019 |

OTHER PUBLICATIONS

Commissioned Project Research (Domestic Feed Pro), Mar. 2013, Ministry of Agriculture, Forestry and Fisheries Agriculture, Forestry and FisheriesResearch Council Secretariat Office of Research Director, Flavor Improved Effect of Pork by Dry Apple Juice, Mar. 2013, with English Abstract, 4 pp.
English Abstract of CN 107095071.
English Abstract of CN 107259179.
English Abstract of CN 107711612.
English Abstract of JP 2016-000707.
English Abstract of JP 2016-199536.
English Abstract of JP-H05-176688.
English Abstract of KR 10-2014-0146307.
English Abstract of Office Action issued on May 9, 2022 in corresponding JP Patent Application No. 2021-530216, 5 pp.
Extended European Search Report issued on Jul. 18, 2022, in corresponding EP Patent Application No. 19890457.5, 6 pp.
In which the skin of apples enhances the burning of calories, improving the diabetes, news, Japan, diabetes networks, Jul. 3, 2012, 5 pp.
Office Action issued on May 9, 2022 in corresponding JP Patent Application No. 2021-530216, 5 pp.
Preparation of ***** to mature Carada in human chemical and phytochemicals (2), research information, Nihon Co., Ltd., CycloChem Co., Ltd. Bio, 2016, Jan. 13, 6 pp.
English Translation of Office Action dated Aug. 27, 2021 issued in corresponding KR Patent Application No. 10-2018-0153029.
Katashima et al., Ursolic acid and mechanisms of actions on adipose and muscle tissue: A systematic review; Etiology and Pathophysiology; Article in Obesity Reviews, Mar. 2017, 12 pp.
Office Action dated Aug. 27, 2021 issued in corresponding KR Patent Application No. 10-2018-0153029.
"Fermentation Production Technology of Amino Acids and Nucleic Acid Substances", edited by Chen Fansheng, pp. 224-225, Chemical Industry Press, Mar. 31, 1993.
Decision of Dismissal of Amendment issued Nov. 27, 2023 of JP Patent Application No. 2021-530216.
Decision of Refusal issued Nov. 27, 2023 of JP Patent Application No. 2021-530216.
Office Action issued Nov. 1, 2023 of CN Patent Application No. 201980079034.5.
Yamamoto et al., "Effects of Feeding a Lower Protein Diet Supplemented with the Apple Pomace on Growth Performance, Nitrogen Excretion and Backfat Thickness in Finishing Pigs" Japanese Pig Meeting Magazine, vol. 40, No. 3, Sep. 2003, pp. 129-134.
English Abstract of CN 102406082.
English Abstract of CN 102578387.
English Abstract of CN 102919607.
English Abstract of CN 105815549.
English Abstract of CN 106819559.
English Abstract of CN 107041460.
English Abstract of KR 10-2004-0093151.
English Abstract of KR 10-2016-0060586.
English Translation of Notification of Reason for Refusal issued in KR 10-2018-0153029, dated Apr. 13, 2021.
Notification of Reason for Refusal issued in KR 10-2018-0153029, dated Apr. 13, 2021.
Chinese Office Action for Chinese Patent Application No. 201980079034.5 dated Mar. 31, 2023.

* cited by examiner

FEED ADDITIVE COMPOSITION AND FEED COMPOSITION COMPRISING THE SAME

CROSS-REFERENCE TO RELATED APPLICATIONS

This application is a national stage application of PCT/KR2019/013203, filed on Oct. 8, 2019, which claims priority to and the benefit of KR 10-2018-0153029 filed on Nov. 30, 2018 both of which are hereby incorporated by reference in their entirety.

TECHNICAL FIELD

The present application relates to a feed additive composition and a feed composition including the same.

BACKGROUND ART

As of the year of 2017, the productivity of domestic pig farms has remained stagnant for years. As a solution to this situation, it has been proposed to increase the shipment weight of fattening pigs by delaying the shipment time thereof, or to improve the competitiveness of farms in the dressing percentage, and accordingly, there is a need to develop feeds suitable for the characteristics of the growth of fattening pigs. The growing of fattening pigs is the last step of growing the same, in which the growth of the muscle is completed and fat is accumulated. Therefore, the growth step of fattening pigs greatly affect, in addition to the dressing percentage, the accumulation of intramuscular fat, for example, reduction of back fat, which is directly related to the quality of pork.

Currently, Paylean from Elanco Inc. has been released as a synthetic product aimed at increasing the dressing percentage and reducing back fat in accordance with the needs of farms, but the product has been classified as a harmful substance due to issues about retention in animal bodies and side effects. Meanwhile, Korean Patent Application Publication No. 10-2016-0119273 discloses a method of treating with glycine compounds or salts thereof and a feed composition including the glycine compounds to reduce the feed conversion ratio of pigs and increase the growth rate of pigs. As such, various studies have been conducted to improve the growth rate of livestock, but are still insufficient.

Under such a background, the inventors of the present disclosure have made efforts to develop feed additives capable of improving farm productivity through, for example, increasing the dressing percentage. As a result, the inventors have confirmed that the feed efficiency and the dressing percentage of livestock can be improved and the level of excessively accumulated back fat can be reduced by additionally feeding ursolic acid and/or maslinic acid derived from the natural product, and based on this result, the present application has been completed.

DESCRIPTION OF EMBODIMENTS

Technical Problem

One objective of the present application is to provide a feed additive composition including ursolic acid or a salt thereof.

Another objective of the present application is to provide a feed composition comprising the feed additive composition.

Other objectives and advantages of the present application will become clearer by the following detailed description along with the appended claims and drawings. Since the content not described in the present specification can be sufficiently recognized and inferred by those skilled in the technical field of the present application or a technical field that is similar thereto, a description thereof will be omitted.

Solution to Problem

Descriptions and embodiments disclosed in the application may also be applied to different descriptions or embodiments. That is, all combinations of the various elements disclosed herein fall within the scope of the present application. In addition, it is not considered that the scope of the present application is limited by the detailed description described below.

An aspect of the present application provides a feed additive composition including ursolic acid or a salt thereof.

As used herein, the term "feed additive" refers to a material added to a feed composition, and may correspond to a supplementary feed according to the Control of Livestock and Fish Feed Act. The feed additive may be used to improve productivity or health of animals or livestock. The productivity of domestic pig farms has remained stagnant for several years, and accordingly, research has been actively conducted on the development of feed additives that contribute to the improvement of pork quality via the increase in dressing percentage and the decrease in back fat. However, there are difficulties in developing feed additives due to issues regarding retention in animal body and side effects.

According to an embodiment, when feed additives containing ursolic acid derived from natural products are additionally fed to growing pigs or fattening pigs, feed efficiency and dressing percentage are improved, and back fat is significantly decreased. Accordingly, the present application may provide a feed additive composition including ursolic acid as an active ingredient.

The term "ursolic acid" as used herein refers to a compound represented by Formula 1 below. The ursolic acid is a kind of pentacyclic triterpenes contained in natural products such as raspberry, cherry, apple gourd, etc., and it has been reported that physiological activities thereof have the effects of antioxidation, insecticide, blood sugar strengthening, anti-aging, etc.

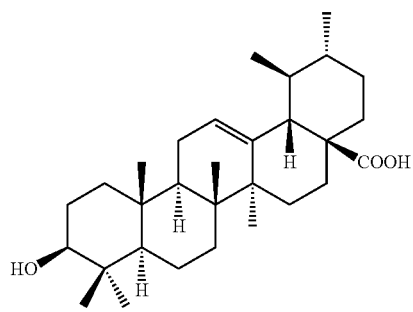

Formula 1

Ursolic acid of the present application may be included in a salt form thereof in a feed additive composition. The ursolic acid may be provided as a salt which is the form being acceptable as a feed component, and may be prepared by any known method. Specific examples thereof are an acid addition salt formed by using inorganic acids such as hydrochloric acid, nitric acid, phosphoric acid, or sulfuric acid; sulphonic acids such as methanesulphonic acids; or an organic acids such as oxalic acid, acetic acid, fumaric acid, malonic acid, maleic acid, malic acid, or succinic acid.

In an embodiment, the feed additive composition of the present application may include the ursolic acid or a salt thereof in an amount of 11000 ppm to 25000 ppm based on the total weight of the feed additive composition. The amount of the ursolic acid or a salt thereof may be, based on the total weight of the feed additive composition, for example, from 11000 ppm to 22000 ppm, from 11000 ppm to 19000 ppm, from 11000 ppm to 16000 ppm, from 11000 ppm to 13000 ppm, from 13000 ppm to 22000 ppm, from 13000 ppm to 19000 ppm, from 13000 ppm to 16000 ppm, from 15000 ppm to 22000 ppm, from 15000 ppm to 19000 ppm, from 15000 ppm to 16000 ppm, from 17000 ppm to 22000 ppm, from 17000 ppm to 19000 ppm, or from 19000 ppm to 22000 ppm, and the amount thereof may be appropriately adjusted according to the type and age of livestock, an application form, or the target effect.

In addition, the feed additive composition of the present application may further include maslinic acid or a salt thereof.

According to an embodiment, when feed additives including ursolic acid and maslinic acid derived from natural products are additionally fed to fattening pigs, feed efficiency and dressing percentage are increased, and in particular, the effect of reduction in back fat is significantly improved compared to a feed additive including ursolic acid. Therefore, the present application may provide a feed additive composition including ursolic acid and maslinic acid as active ingredients.

As used herein, the term "maslinic acid" refers to a compound represented by Formula 2 below. The maslinic acid is a kind of pentacyclic triterpenes contained in natural products such as *Schisandra chinensis* and loquat leaf, and the like, and it has been reported that physiological activities thereof, include antioxidation, anti-aging, anti-inflammation, and the like.

Formula 2

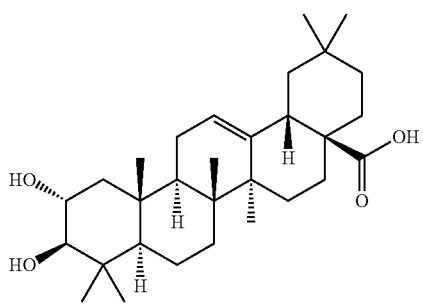

Like ursolic acid, the maslinic acid of the present application may be included in a salt form thereof in a feed additive composition. The maslinic acid may be provided in the form of a salt that is acceptable for use as a feed component, and a specific example of the salt is the same as described in connection with ursolic acid.

In an embodiment, the feed additive composition of the present application may include the maslinic acid or a salt thereof in an amount of 40 ppm to 10000 ppm based on the total weight of the feed additive composition. The amount of the maslinic acid or a salt thereof may be, for example, based on the total weight of the feed additive composition, from 40 ppm to 9000 ppm, from 40 ppm to 8000 ppm, from 40 ppm to 7000 ppm, from 40 ppm to 6000 ppm, from 40 ppm to 5000 ppm, from 40 ppm to 4000 ppm, from 40 ppm to 3000 ppm, from 40 ppm to 2000 ppm, from 40 ppm to 1000 ppm, from 40 ppm to 5000 ppm, from 40 ppm to 2500 ppm, from 40 ppm to 2000 ppm, from 40 ppm to 1500 ppm, or from 40 to 1000 ppm, for example, from 100 ppm to 5000 ppm, from 100 ppm to 4000 ppm, from 100 ppm to 3000 ppm, from 100 ppm to 2000 ppm, from 100 ppm to 1000 ppm, from 200 ppm to 2500 ppm, from 200 ppm to 2000 ppm, from 200 ppm to 1500 ppm, or from 200 ppm to 1000 ppm, and the amount thereof may be appropriately adjusted according to the type and age of livestock, an application form, or the target effect.

In an embodiment, the ursolic acid and the maslinic acid of the present application may be included in a weight ratio of 1:1 to 3000:1. The weight ratio of the ursolic acid to the maslinic acid may be, for example, from 1:1 to 2500:1, from 1:1 to 2000:1, from 1:1 to 1500:1, from 1:1 to 1000:1, from 1:1 to 500:1, from 1:1 to 400:1, from 1:1 to 300:1, from 1:1 to 200:1, from 1:1 to 100:1, from 1:1 to 90:1, from 1:1 to 80:1, from 1:1 to 70:1, from 1:1 to 60:1, from 1:1 to 50:1, from 1:1 to 40:1, from 1:1 to 30:1, from 1:1 to 20:1, or from 1:1 to 10:1. However, the weight ratio thereof may be appropriately changed.

The feed additive composition of the present application may be prepared in a powder or granular form, and according to the purpose, may further include any one or more of organic acids such as citric acid, fumaric acid, adipic acid, lactic acid, and malic acid; phosphate salts such as sodium phosphate, potassium phosphate, acidic pyrophosphate, or polyphosphate; or natural antioxidants such as polyphenol, catechin, alpha-tocopherol, rosemary extract, vitamin C, green tea extract, licorice extract, chitosan, tannic acid, or phytic acid. The feed additive composition of the present application may be formulated in the form of a conventional feed, and may include feed components of the related art together.

The feed additive composition of the present application may further include grains, for example, wheat, oats, barley, corn and rice, each of which is ground or crushed; vegetable protein feeds, for example, feeds including, as a major component, rapeseed, soybean and sunflower; animal protein feeds, for example, blood meal, meat meal, bone meal and fish meal; sugar and dairy products, for example, a dry component including various kinds of milk powder and whey powder. Besides, the feed additive composition may further include a nutritional supplement, a digestion and absorption enhancer, a growth promoter, and the like.

The feed additive composition of the present application may be administered to an animal alone or in combination with other feed additives in an edible carrier. In addition, the feed additive composition may be easily administered to an animal, as a top dressing, directly being mixed with feeds, or an oral formulation separate from feeds. When the feed additive composition is administered separately from the feeds, as well known in the art, the feed additive composition may be combined with a pharmaceutically acceptable edible carrier to be provided in the form of an immediate release or sustained release formulation. Such edible carriers may be solid or liquid, for example, corn starch, lactose, sucrose, soy flakes, peanut oil, olive oil, sesame oil and propylene glycol. When a solid carrier is used, the feed additive composition may be in the form of a tablet, capsule, powder, troche or lozenge, or a top dressing in a non-dispersible form. When a liquid carrier is used, the feed additive composition may be in the form of a gelatin soft capsule, a syrup, a suspension, an emulsion, or a solution.

The feed additive composition of the present application may contain, for example, a preservative, a stabilizer, a wetting or emulsifying agent, a solution accelerator, and the like. The feed additive composition may be used by being immersed, sprayed, or mixed in animal feeds.

The feed additive composition according to the present application may be applied to a plurality of diets for animals including mammals and poultry. The mammals may include pigs, cows, sheep, goats, laboratory rodents, or pet animals (for example, dogs and cats), and the poultry may include chickens, turkeys, ducks, geese, pheasants, quail, and the like.

Another aspect of the present application provides a feed composition including the feed additive composition of the present application.

The term "feed composition" used herein refers to feeds fed to animals. The feed composition refers to a material that supplies organic or inorganic nutrients that are needed to maintain the life of an animal or produce meat, milk, etc. The feed composition may include the feed additive composition of the present application, and may further include nutrients that are needed to maintain the life of animals or produce meat, milk, and the like.

The amount of the feed additive composition in the feed composition of the present application may be appropriately adjusted according to the type and age of livestock, an application form, or the target effect, and may be from 0.01% (w/w) to 1% (w/w), from 0.01% (w/w) to 0.5% (w/w), or from 0.15% (w/w) to 0.5% (w/w).

In an embodiment, the feed composition of the present application may include the ursolic acid or a salt thereof in an amount of 10 ppm to 300 ppm based on the total weight of the feed composition. The amount of the ursolic acid or a salt thereof may be, based on the total weight of the feed composition, for example, from 10 ppm to 90 ppm, from 10 ppm to 80 ppm, from 10 ppm to 70 ppm, from 10 ppm to 60 ppm, from 10 ppm to 50 ppm, from 10 ppm to 40 ppm, from 10 ppm to 30 ppm, or from 10 ppm to 20 ppm, and the amount thereof may be appropriately adjusted according to the type and age of livestock, an application form, or the target effect.

In an embodiment, the feed composition of the present application may include the maslinic acid or a salt thereof in an amount of 1 ppb to 100 ppb based on the total weight of the feed composition. The amount of the maslinic acid or a salt thereof may be, based on the total weight of the feed composition, for example, from 1 ppb to 90 ppb, from 1 ppb to 80 ppb, from 1 ppb to 70 ppb, from 1 ppb to 60 ppb, from 1 ppb to 50 ppb, from 1 ppb to 45 ppb, from 1 ppb to 40 ppb, from 1 ppb to 35 ppb, from 1 ppb to 30 ppb, from 1 ppb to 25 ppb, from 1 ppb to 20 ppb, or may be from 1 ppb to 10 ppb, and the amount thereof may be appropriately adjusted according to the type and age of livestock, an application form, or the target effect.

The feed composition of the present application may further include any one or more essential amino acids selected from the group consisting of lysine, threonine, tryptophan, methionine, and valine.

According to an embodiment, when the feed additive composition including ursolic acid and maslinic acid is fed to fattening pigs together with an essential amino acid such as lysine, feed efficiency and dressing percentage are further increased. Accordingly, the present application may provide a feed composition further including an essential amino acid in terms of enhancing efficacy.

In an embodiment, the feed composition of the present application may include the essential amino acid in an amount of 0.05% (w/w) to 5% (w/w), based on the total weight of the feed composition. The amount of the essential amino acid may be, based on the total weight of the feed composition, for example, from 0.05% (w/w) to 4% (w/w), from 0.05% (w/w) to 3% (w/w), from 0.05% (w/w) to 2% (w/w), from 0.05% (w/w) to 1% (w/w), from 0.1% (w/w) to 4% (w/w), from 0.1% (w/w) to 3% (w/w), from 0.1% (w/w) to 2% (w/w), from 0.1% (w/w) to 1% (w/w), from 0.5% (w/w) to 4% (w/w), from 0.5% (w/w) to 3% (w/w), from 0.5% (w/w) to 2% (w/w), or from 0.5% (w/w) to 1% (w/w).

For administration, the feed composition of the present application may further include, in addition to the feed additive composition, at least one of: organic acids such as citric acid, fumaric acid, adipic acid, lactic acid, and the like; phosphates such as potassium phosphate, sodium phosphate, polymerized phosphates, and the like; natural antioxidants such as polyphenol, catechin, tocopherol, vitamin C, green tea extract, chitosan, tannic acid, and the like, and if needed, may include other additives of the related art, such as anti-influenza agent, a buffer solution, a bacteriostatic agent, and the like, each of which is used in the mixed form therewith In an embodiment, the feed composition of the present application may be formulated into injectable formulations, such as aqueous solutions, suspensions, or emulsions; capsules; granules; or tablets and the like by additionally adding a diluent, a dispersant, a surfactant, a binder, or a lubricant. In an embodiment, the feed composition of the present application may include, as a major component, vegetable protein feeds such as wheat, barley, corn, each of which is ground or crushed; animal protein feeds such as blood meal, meat meal, or fish meal; animal fat; or vegetable fat. Together with the major component, the feed composition of the present application may further include, as an auxiliary component, various supplements, such as amino acids, inorganic salts, vitamins, antioxidants, antifungal agents, or antibacterial agents; growth promoters; digestive absorption promoters; or disease prevention agents.

The feed composition of the present application may be mixed in an amount of about 10 g to about 500 g, for example, about 10 g to about 100 g per 1 kg of livestock feeds on a dry weight basis, and may be completely mixed and then supplied as a mesh, or may be subject to a pelletizing, expanding, or extrusion process through an additional processing process.

Advantageous Effects of Disclosure

The feed additive composition according to the present disclosure can increase feed efficiency and dressing percentage of livestock, and can significantly reduce back fat.

Therefore, the feed additive composition according to the present application or the feed composition including the same may contribute to improving productivity and quality of livestock.

MODE OF DISCLOSURE

Hereinafter, the present disclosure will be described in more detail through Examples. However, these embodiments are provided to exemplarily describe the present disclosure, and the scope of the present disclosure is not limited to these embodiments.

Experimental Example 1. Specification Test in the Step of Growing Pigs According to the Feeding of Feed Additives In the present Experimental Example, it was determined whether the feed additives including ursolic acid had an effect on feed efficiency. In the present Experimental Example, the test livestock was a total of 288 Durocx YorkshirexLandrace three-way crossbreeding growing pigs, and the average weight thereof at the start of the test was 37.73±2.14 kg. The specification test was conducted for 36 days at a Farm in Wanju-gun, South Korea, which is a farm of CJ Dondon Farm, a subsidiary of CJ CheilJedang. As a test design, a CJ CheilJedang base feed treatment group (Control) and a test feed treatment group (Example 1) in which 25 ppm of ursolic acid was added to the base feed based on the total weight of the feed were used. That is, the test feed treatment group is a treatment group in which the feed additive according to the present Experimental Example is added to a base feed, and the feed additive including ursolic acid in an amount of 17000 ppm based on the total weight of the feed additive was used therefor. The feed additive was prepared by measuring the amount of ursolic acid in an existing natural product and then adjusting the amount of ursolic acid based on the measurements, and, if needed, adding ursolic acid extracted from a natural product. Four repeated tests were performed for each treatment group, and 24 samples were completely randomly designed for each test group. As a base feed, a feed for livestock containing 2,510 kcal net energy (NE)/kg, 17.00 wt % of protein, and 0.93 wt % of lysine based on the national research council (NRC) standard, was used. The feeds were prepared in the form of powdered feeds and allowed to be fed freely, and water was provided using an automatic water feeder. Thereafter, the weight and feed intake of the test livestock were measured at each time point to calculate an average daily gain (ADG), an average daily feed intake (ADFI), and feed conversion ratio (FCR). The FCR refers to a ratio of feed weight to weight gain, and significance of the averages of the treatment groups was identified using the general linear model procedure program of SAS 1996.

Table 1 shows the measurements of ADG, ADFI, and feed efficiency of growing pigs fed with the base feed or test feed for 36 days.

TABLE 1

| | TREATMENT GROUP | |
|---|---|---|
| | CONTROL Base Feed | EXAMPLE 1 Base Feed + Ursolic acid (25 ppm) |
| BODY WEIGHT (kg) | | |
| START | 37.9 ± 2.5 | 37.6 ± 1.7 |
| WEEK 2 | 51.6 ± 3.2 | 51.2 ± 2.2 |
| WEEK 5 (END) | 71.1 ± 2.9 | 72.4 ± 2.5 |
| WEEK 0-2 | | |
| ADG, g | 978 | 975 |
| ADFI, g | 1,956 | 1,966 |
| FCR | 2.01 | 2.02 |

TABLE 1-continued

| | TREATMENT GROUP | |
|---|---|---|
| | CONTROL Base Feed | EXAMPLE 1 Base Feed + Ursolic acid (25 ppm) |
| WEEK 2-5 | | |
| ADG, g | 887 | 961 |
| ADFI, g | 2,505 | 2,368 |
| FCR | 2.82 | 2.47 |
| WEEK 0-5 | | |
| ADG, g | 922 | 966 |
| ADFI, g | 2,291 | 2,212 |
| FCR | 2.48 | 2.29 |

As shown in Table 1, on the 36th day after the base feed or test feed was fed, the ADG of the growing pigs according to Example 1 was increased by about 5% compared to the control, and the feed efficiency of the growing pigs according to Example 1 was also increased by about 8.4% compared to the control. From the results of these experiments, it could be seen that the feed additive containing ursolic acid promotes the growth of the growing pigs, and also increases the weight gain with respect to feed weight, i.e., feed efficiency.

Experimental Example 2. Results of Specification Test in the Step of Growing Pigs/Fattening Pigs According to the Feeding of Feed Additive In the present Experimental Example, it was determined whether the feed additive including ursolic acid and/or maslinic acid has an effect on feed efficiency, a dressing percentage, and a level of a back fat. The test livestock in the present Experimental Example were a total of 120 Durocx YorkshirexLandrace three-way crossbreeding growing pigs/fattening pigs, and the average weight thereof at the start of the test was 43.3 kg±0.9 kg. The specification test was conducted on a test farm belonging to the Chungnam National University (South Korea) for 67 days by service evaluation. As shown in Table 2 below, as a test design, CJ CheilJedang base feed treatment group (control group); test feed treatment groups (Example 2 or 3) in which 25 ppm or 50 ppm of ursolic acid was added to the base feed based on the total weight of the feed; and a test feed treatment group (Example 4) in which 25 ppm of ursolic acid and 10 ppb of maslinic acid were added to the base feed based on the total weight of the feed. The test feed treatment group is a treatment group in which the feed additive according to the present Experimental Example is added to a base feed, and the feed additive including 17,000 ppm of ursolic acid or 5,500 ppm of maslinic acid based on the total weight of the feed additive was used therefor. The feed additive was prepared by measuring the amount of ursolic acid or maslinic acid in an existing natural product and then adjusting the amount thereof based on the measurements, and, if needed, adding ursolic acid or maslinic acid extracted from a natural product. Six repeated tests were performed for each treatment group, and 4 samples were completely randomly designed for each test group. As a base feed, a feed for livestock containing 2,510 kcal net energy (NE)/kg, 17.00 wt % of protein, and 0.93 wt % of lysine based on the NRC standard, was used. The feeds were prepared in the form of powdered feeds and allowed to be fed freely, and water was provided using an automatic water feeder. Thereafter, the weight and feed intake of the test livestock were measured at each time point to calculate the ADG, ADFI, and feed efficiency thereof, and after slaughtering the test livestock, the dressing percentage and the level of back fat were measured (NE). In addition, the general linear model procedure program of SAS 1996 was used to assay the significance of the averages of the treatment groups.

TABLE 2

| COMPONENTS | TREATMENT GROUP | | | |
|---|---|---|---|---|
| | CONTROL | EXAMPLE 2 | EXAMPLE 3 | EXAMPLE 4 |
| | Base Feed | Base Feed | Base Feed | Base Feed |
| | — | Ursolic acid (25 ppm) | Ursolic acid (50 ppm) | Ursolic acid (25 ppm) |
| | — | — | — | Maslinic acid (10 ppb) |

Table 3 shows the measurements of feed efficiency, dressing percentage, and level of back fat of growing pigs/fattening pigs fed with the base feed or test feed for 67 days.

TABLE 3

| | TREATMENT GROUP | | | |
|---|---|---|---|---|
| | CONTROL | EXAMPLE 2 | EXAMPLE 3 | EXAMPLE 4 |
| SPECIFICATION RESULTS | | | | |
| ADG, kg/d | 0.987 | 1.033 | 1.034 | 1.032 |
| ADFI, kg/d | 3.118 | 3.094 | 3.035 | 3.056 |
| G:F, kg/kg | 0.316 | 0.334 | 0.341 | 0.338 |
| FCR, ratio | 3.159 | 2.995 | 2.935 | 2.961 |
| SLAUGHTER/SHIPMENT RESULTS | | | | |
| LIVE BODY WEIGHT, kg | 108.30 | 108.10 | 108.30 | 108.70 |
| CARCASS BODY WEIGHT, kg | 83.59 | 85.33 | 86.27 | 86.17 |
| DRESSING PERCENTAGE, % | 77.20 | 78.92 | 79.66* | 79.29* |
| BACK FAT, mm | 24.80 | 23.88 | 23.64* | 23.50* |
| DECREASE IN BACK FAT, mm | — | −0.92 | −1.16 | −1.30 |
| INCREASE IN DRESSING PERCENTAGE, % | — | 1.72 | 2.46 | 2.1 |

As shown in Table 3, on the 67th day after the base feed or test feed was fed, the growing pigs and the fattening pigs according to Examples 2, 3, or 4 all showed an increase in ADG, FCR, and dressing percentage, and a decrease in the back fat, as compared with the control. In particular, in terms of the dressing percentage and the reduction of the back fat, the growing pigs and fattening pigs according to Examples 3 and 4 showed a significant difference from the control (*, $p<0.05$).

Specifically, in the growing pigs and fattening pigs according to Example 2 in which ursolic acid was additionally fed, feed efficiency was increased and the dressing percentage was increased and the back fat was reduced. In addition, in the case of the growing pigs and fattening pigs of Example 3, compared to the control, the dressing percentage was increased by about 2.46% and the back fat was decreased by about 1.16 mm. These results are better than those of Example 2, and thus it could be seen that the dressing percentage is increased and the back fat is decreased depending on the feed amount of ursolic acid.

In addition, in the case of the growing pigs and fattening pigs of Example 4, which were fed with ursolic acid and maslinic acid, compared to the control, the dressing percentage was increased by 2.1%, and the back fat was decreased by 1.30 mm. As described above, these results are better than the effect of increasing the dressing percentage and reducing back fat of Example 2, and particularly, in the aspect of the reduction of back fat, are better than even Example 3 in which a large amount of ursolic acid is supplied. Therefore, it can be seen that the feeding of ursolic acid and maslinic acid further enhance the effect of increasing the dressing percentage and reducing the back fat.

Experimental Example 3. Results of Specification Test in the Step of Fattening Pigs According to the Feeding of Feed Additive The present Experimental Example was conducted to identify the feed efficiency, the increase in the dressing percentage, and the decrease in the back fat when an essential amino acid component was added to the feed additive of Experimental Example 2. The test livestock in the present Experimental Example were a total of 228 Duroc×Yorkshire×Landrace three-way crossbreeding fattening pigs, and the average weight thereof at the start of the test was 70.6 kg±2.5 kg. The specification test was conducted for 42 days at a Farm in Wanju-gun, South Korea, which is a farm of CJ Dondon Farm, a subsidiary of CJ CheilJedang. As shown in Table 4 below, as a test design, CJ CheilJedang base feed treatment group (control group); a test feed treatment group (Example 5) in which 50 ppm of ursolic acid and 20 ppb of maslinic acid were added to the base feed; and a test feed treatment group (Example 6) in which 0.13% (w/w) of lysine was added to the test feed of Example 5, were used. The test feed treatment group is a treatment group in which the feed additive according to the present Experimental Example is added to a base feed, and the feed additive including 17,000 ppm of ursolic acid or 5,500 ppm of maslinic acid based on the total weight of the feed additive was used therefor. The feed additive was prepared by measuring the amount of ursolic acid or maslinic acid in an existing natural product and then adjusting the amount thereof based on the measurements, and, if needed, adding ursolic acid or maslinic acid extracted from a natural product. In addition, 0.13% of lysine was added to the test feed of Example 5 to prepare the test feed of Example 6. Four repeated tests were performed for each treatment group, and 24 samples were completely randomly designed for each test group. As a base feed, a feed for livestock containing 2,510 kcal net energy (NE)/kg, 17.00 wt % of protein, and 0.93 wt % of lysine based on the national research council (NRC) standard, was used. The feeds were prepared in the form of powdered feeds and allowed to be fed freely, and water was provided using an automatic water feeder. Thereafter, the weight and feed intake of the test livestock were measured at each time point to calculate the ADG, ADFI, and feed efficiency thereof, and after slaughtering the test livestock, the dressing percentage and the level of back fat were measured (NE). In addition, the general linear model procedure program of SAS 1996 was used to assay the significance of the averages of the treatment groups.

TABLE 4

| | TREATMENT GROUP | | |
|---|---|---|---|
| | CONTROL | EXAMPLE 5 | EXAMPLE 6 |
| COMPONENTS | Base Feed | Base Feed | Base Feed |
| | — | Ursolic acid (50 ppm) | Ursolic acid (50 ppm) |
| | — | Maslinic acid (20 ppb) | Maslinic acid (20 ppb) |
| | — | — | Lysine (0.13%) |

Table 5 shows the measurements of feed efficiency, dressing percentage, and level of back fat of fattening pigs fed with the base feed or test feed for 42 days.

TABLE 5

| | TREATMENT GROUP | | |
|---|---|---|---|
| | CONTROL | EXAMPLE 5 | EXAMPLE 6 |
| BW, kg | | | |
| START BODY WEIGHT | 70.29 | 70.25 | 71.26 |
| END BODY WEIGHT | 99.44 | 99.44 | 103.93 |
| SPECIFICATION RESULTS | | | |
| ADG, g/d | 786 | 786 | 883 |
| ADFI, g/d | 2,575 | 2,514 | 2,649 |
| FCR, ratio | 3.30 | 3.20 | 3.01 |
| SLAUGHTER/SHIPMENT RESULTS | | | |
| NUMBER OF HEADS, n | 26 | 27 | 33 |
| LIVE BODY WEIGHT, kg | 113.3 | 110.5* | 111.8 |
| CARCASS BODY WEIGHT, kg | 84.81 | 83.85 | 85.24 |
| DRESSING PERCENTAGE, % | 74.82 | 75.87* | 76.27* |

TABLE 5-continued

| | TREATMENT GROUP | | |
|---|---|---|---|
| | CONTROL | EXAMPLE 5 | EXAMPLE 6 |
| BACK FAT, mm | 26.38 | 24.15 | 25.76 |
| DECREASE IN BACK FAT, mm | — | −2.23 | −0.62 |
| INCREASE IN DRESSING PERCENTAGE, % | — | 1.05 | 1.45 |

As shown in Table 5, on the 42nd day after feeding the base feed or the test feed, in the case of the fattening pigs of Example 5, not only the feed efficiency was improved, but also the dressing percentage was increased by 1.05%, and the back fat was reduced by about 2.23 mm, compared to the control. That is, the effect of feeding ursolic acid and maslinic acid, which was identified in Experimental Example 2, was re-confirmed.

Specifically, in the fattening pigs according to Example 6 in which lysine was additionally fed, feed efficiency was increased and the dressing percentage was increased and the back fat was reduced. For example, in the case of the fattening pigs of Example 6, the dressing percentage was increased by about 1.45% and the back fat was decreased by about 0.62 mm, compared to the control. In particular, the effect of improving the dressing percentage of Example 6 was significantly improved compared to the result of Example 5, and the effect of reducing back fat was also determined to be a significant reduction effect when the improved dressing percentage was comprehensively considered. Therefore, it can be seen that the addition of essential amino acid components such as lysine contributes to the enhancement of the effects of ursolic acid and maslinic acid fed as feed additives.

The above description of the present disclosure is for illustration, and it will be understood by those skilled in the art that the present disclosure can be easily modified into other specific forms without changing the technical concept or essential features of the present disclosure. Therefore, it should be understood that the embodiments described above are examples in all aspects and are not limited thereto.

The invention claimed is:

1. A method of improving productivity or quality of a non-human animal, the method comprising:
    administering to a non-human animal a feed composition comprising ursolic acid, or a salt thereof, as an active ingredient in an amount of 10 ppm to 300 ppm based on the total weight of the feed composition, wherein the improving of productivity or quality of a non-human animal is an increase in body weight, an increase in feed efficiency, an increase in dressing percentage, and a decrease in back fat.

2. The method of claim 1, wherein the feed composition further comprises maslinic acid, or a salt thereof.

3. The method of claim 2, wherein the feed additive composition comprises maslinic acid, or a salt thereof, in an amount of 1 ppb to 100 ppb based on the total weight of the feed composition.

4. The method of claim 2, wherein a weight ratio of the ursolic acid to the maslinic acid is 1:1 to 3000:1.

5. The method of claim 1, wherein the feed composition further comprises one or more essential amino acids selected from the group consisting of lysine, threonine, tryptophan, methionine, and valine.

6. The method of claim 5, wherein the feed composition comprises the essential amino acids in an amount of 0.05% (w/w) to 5% (w/w) based on the total weight of the feed composition.

7. A method of feeding a non-human animal, the method comprising:
  feeding a non-human animal with a feed composition comprising ursolic acid, or a salt thereof, as an active ingredient in an amount of 10 ppm to 300 ppm based on the total weight of the feed composition.

8. The method of claim 7, wherein the feed composition further comprises maslinic acid, or a salt thereof.

9. The method of claim 8, wherein the feed additive composition comprises maslinic acid, or a salt thereof, in an amount of 1 ppb to 100 ppb based on the total weight of the feed composition.

10. The method of claim 8, wherein a weight ratio of the ursolic acid to the maslinic acid is 1:1 to 3000:1.

11. The method of claim 7, wherein the feed composition further comprises one or more essential amino acids selected from the group consisting of lysine, threonine, tryptophan, methionine, and valine.

12. The method of claim 11, wherein the feed composition comprises the essential amino acids in an amount of 0.05% (w/w) to 5% (w/w) based on the total weight of the feed composition.

* * * * *